United States Patent
Petermann et al.

(10) Patent No.: US 10,526,421 B2
(45) Date of Patent: Jan. 7, 2020

(54) ESTERIFIED CELLULOSE ETHERS OF LOW ACETONE-INSOLUBLE CONTENT

(71) Applicant: Dow Global Technologies LLC, Midland, MI (US)

(72) Inventors: Oliver Petermann, Hamburg (DE); Matthias Knarr, Nienburg/Weser (DE); Matthias Sprehe, Walsrode (DE)

(*) Notice: Subject to any disclaimer, the term of this patent is extended or adjusted under 35 U.S.C. 154(b) by 206 days.

(21) Appl. No.: 15/503,600

(22) PCT Filed: Aug. 18, 2015

(86) PCT No.: PCT/US2015/045596
§ 371 (c)(1),
(2) Date: Feb. 13, 2017

(87) PCT Pub. No.: WO2016/032791
PCT Pub. Date: Mar. 3, 2016

(65) Prior Publication Data
US 2017/0240654 A1     Aug. 24, 2017

Related U.S. Application Data

(60) Provisional application No. 62/042,410, filed on Aug. 27, 2014.

(51) Int. Cl.
| | |
|---|---|
| C08B 13/00 | (2006.01) |
| C09D 101/32 | (2006.01) |
| C08L 1/32 | (2006.01) |
| A61K 9/48 | (2006.01) |
| A61K 47/38 | (2006.01) |
| A61K 9/14 | (2006.01) |
| A61K 9/20 | (2006.01) |

(52) U.S. Cl.
CPC ............ *C08B 13/00* (2013.01); *A61K 9/4816* (2013.01); *C08L 1/32* (2013.01); *C09D 101/32* (2013.01); *A61K 9/146* (2013.01); *A61K 9/2054* (2013.01); *A61K 47/38* (2013.01)

(58) Field of Classification Search
CPC .......... C08B 13/00; C08L 1/32; C09D 101/32
See application file for complete search history.

(56) References Cited

U.S. PATENT DOCUMENTS

| | | | | |
|---|---|---|---|---|
| 2,099,502 | A | 11/1937 | Stockdale | |
| 4,226,981 | A * | 10/1980 | Onda | A61K 9/2866 424/480 |
| 4,365,060 | A | 12/1982 | Onda et al. | |
| 7,255,878 | B1 * | 8/2007 | Lahav | A61K 9/2031 424/400 |
| 8,710,105 | B2 * | 4/2014 | Son | A61K 9/4816 424/451 |

FOREIGN PATENT DOCUMENTS

| | | |
|---|---|---|
| EP | 2476439 A1 | 7/2012 |
| JP | 06256171 A | 9/1994 |
| WO | WO-2003/063831 A2 | 8/2003 |
| WO | 2005115330 A2 | 12/2005 |
| WO | 2011159626 A1 | 12/2011 |
| WO | 2013148154 A1 | 10/2013 |
| WO | 2013154607 A1 | 10/2013 |
| WO | 2014031422 A1 | 2/2014 |
| WO | WO-2014/031446 A1 | 2/2014 |
| WO | 2015126576 A1 | 8/2015 |

OTHER PUBLICATIONS

Shin Etsu Aqoat (published in 2005).*
Communication from European Patent Office dated Aug. 21, 2017; for EP Application No. 15760541.1-1302; pursuant to Rules 161 and 162 EPC.

* cited by examiner

*Primary Examiner* — Pancham Bakshi

(57) ABSTRACT

Esterified cellulose ethers which have i) as ester groups aliphatic monovalent acyl groups or groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and ii) a content of not more than 0.85 weight percent acetone-insoluble esterified cellulose ether particles, when the esterified cellulose ether is present in a mixture of 12.5 weight parts of esterified cellulose ether and 87.5 weight parts of acetone at 21° C., the weight percent acetone-insoluble esterified cellulose ether particles being based on the total weight of the esterified cellulose ether, wherein iii) not more than 14 percent of the acetone-insoluble esterified cellulose ether particles have a particle size of more than 90 micrometers.

14 Claims, 1 Drawing Sheet

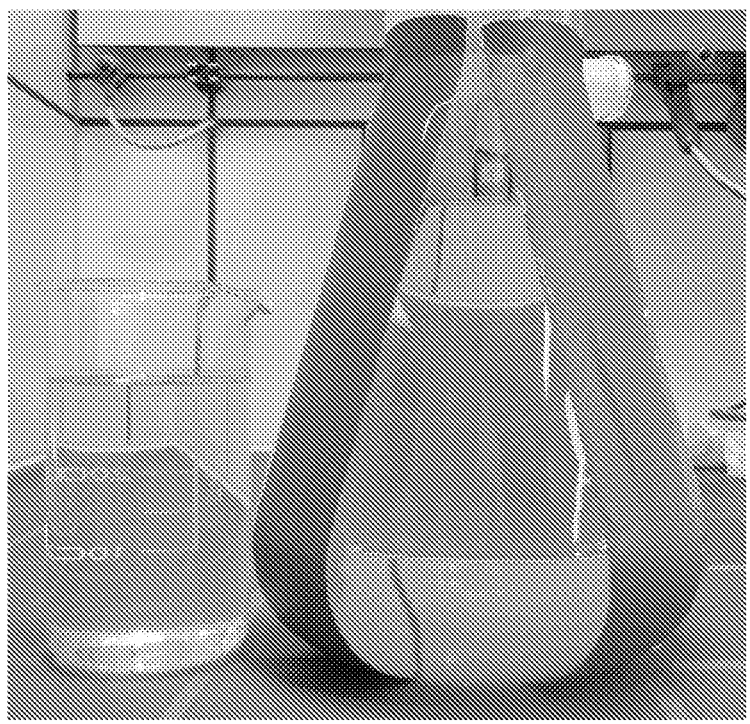
1B 1A

ESTERIFIED CELLULOSE ETHERS OF LOW ACETONE-INSOLUBLE CONTENT

FIELD

This invention concerns esterified cellulose ethers of low acetone-insoluble content, and solid dispersions of an active ingredient in such esterified cellulose ethers, as well as liquid compositions, coated dosage forms and capsules comprising such esterified cellulose ethers and a process for producing esterified cellulose ethers.

INTRODUCTION

Esters of cellulose ethers, their uses and processes for preparing them are generally known in the art. Various known esterified cellulose ethers are useful as enteric polymers for pharmaceutical dosage forms, such as hydroxypropyl methyl cellulose acetate succinate (HPMCAS). Enteric polymers are those that are resistant to dissolution in the acidic environment of the stomach. Dosage forms coated with such polymers protect the drug from inactivation or degradation in the acidic environment or prevent irritation of the stomach by the drug.

U.S. Pat. No. 4,365,060 discloses enterosoluble capsules which are said to have excellent enterosolubility behavior. The enterosoluble capsules are shaped with an ester of a cellulose ether that is esterified with acidic succinyl groups and aliphatic monovalent acyl groups. It is recommended that the cellulose ethers used for esterification have a molecular weight in the range from about 5000 to 200,000 to obtain adequate plasticity.

International Patent Application WO2014/031422 discloses hydroxyalkyl methyl cellulose acetate succinates having a weight average molecular weight $M_w$ of from 80,000 Dalton to 350,000 Dalton and a low turbidity as 1.5 weight percent solution in acetone. A low turbidity is desirable in transparent films or coatings.

International Patent Applications WO 2005/115330, WO 2011/159626, WO2013/154607 and WO2014/031422 relate to the use of HPMCAS for improving the solubility of poorly water-soluble drugs. A large number of presently known drugs have a low solubility in water, and thus complex techniques are required to prepare a dosage form. One method includes dissolving such drug together with a HPMCAS in acetone and to spray-dry the solution. The HPMCAS is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

However, spray-drying a solution of a drug and an esterified cellulose ether such as HPMCAS in acetone is a complex operation. A spray system that is not working optimally increases the costs of the spray-drying operation to a large degree. When spray nozzles become partially blocked, spraying efficiency is degraded. It is generally known that factors that may cause clogging are particle agglomeration and build-up of material on the inside and outer edges of the orifice of the spray nozzles. To reduce clogging of spray nozzles, it has been known for a long time to provide spraying systems with strainers in the suction line or the pressure line of the spraying system, such as disclosed in U.S. Pat. No. 2,099,502. Spray nozzles with built-in strainers are also known. However, regular cleaning of the strainers is required to enable proper operation of the spray system over an extended period of time.

In view of the complexity of spray-drying a solution of a drug and an esterified cellulose ether, such as a drug and HPMCAS in acetone, there is a long-felt need to find a way of decreasing insoluble cellulose ether particles in solvent systems for spray-drying applications, for example when using acetone as a solvent, e.g. by reducing or preventing agglomerates or lumps of esterified cellulose ether particles in the solvent system.

SUMMARY

Surprisingly, it has been found that a new esterified cellulose ether having a very low amount of acetone-insoluble esterified cellulose ether particles can be produced when a cellulose ether is esterified with an aliphatic monocarboxylic acid anhydride and/or a dicarboxylic acid anhydride in the presence of an aliphatic carboxylic acid as a diluent, when the resulting reaction product mixture is optionally diluted, the optionally diluted reaction product mixture is filtered, and the esterified cellulose ether is precipitated from the filtered reaction product mixture.

Accordingly, one aspect of the present invention is an esterified cellulose ether that has i) as ester groups aliphatic monovalent acyl groups or groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and ii) a content of not more than 0.85 weight percent acetone-insoluble esterified cellulose ether particles, when the esterified cellulose ether is present in a mixture of 12.5 weight parts of esterified cellulose ether and 87.5 weight parts of acetone at 21° C., the weight percent acetone-insoluble esterified cellulose ether particles being based on the total weight of the esterified cellulose ether, wherein iii) not more than 14 percent of the acetone-insoluble esterified cellulose ether particles have a particle size of more than 90 micrometers, the percentage being based on the total number of acetone-insoluble esterified cellulose ether particles.

Another aspect of the present invention is a process for producing an esterified cellulose ether which comprises the steps of I. esterifying a cellulose ether with an aliphatic monocarboxylic acid anhydride or a dicarboxylic acid anhydride or combination thereof in the presence of an aliphatic carboxylic acid to produce a reaction product mixture comprising an esterified cellulose ether and the aliphatic carboxylic acid, II. optionally diluting the reaction product mixture obtained in step I, III. filtering the optionally diluted reaction product mixture, and IV. precipitating the esterified cellulose ether from the filtered reaction product mixture by contacting the filtered reaction product mixture with water.

Another aspect of the present invention is a composition comprising a liquid diluent and at least one esterified cellulose ether as described above.

Yet another aspect of the present invention is a solid dispersion comprising at least one active ingredient in at least one esterified cellulose ether as described above.

Yet another aspect of the present invention is a dosage form which is coated with the esterified cellulose ether as described above.

Yet another aspect of the present invention is a capsule shell which comprises the esterified cellulose ether as described above.

BRIEF DESCRIPTION OF DRAWINGS

FIG. 1 is a photographical representation of two reaction product mixtures obtained by esterifying hydroxypropyl methylcellulose with acetic anhydride and succinic anhydride in the presence of sodium acetate and acetic acid and subsequent dilution with acetic acid. Part 1A of FIG. 1 represents the diluted reaction product mixture before filtration. Part 1B of FIG. 1 represents a photograph of the diluted reaction product mixture after filtration.

DETAILED DESCRIPTION

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.20 to 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, most preferably from 1.2 to 2.2 and particularly from 1.6 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention has as ester groups aliphatic monovalent acyl groups or groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are —C(O)—CH$_2$—CH$_2$—COOA, such as —C(O)—CH$_2$—CH$_2$—COOH or —C(O)—CH$_2$—CH$_2$—COO$^-$Na$^+$,
C(O)—CH=CH—COOA, such as —C(O)—CH=CH—COOH or —C(O)—CH=CH—COO$^-$Na$^+$, or
C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA the carbonyl group and the carboxylic group are preferably arranged in ortho-positions.

Preferred esterified cellulose ethers are i) HPMCXY and HPMCX, wherein HPMC is hydroxypropyl methyl cellulose, X is A (acetate), or X is B (butyrate) or X is Pr (propionate) and Y is S (succinate), Y is P (phthalate) or Y is M (maleate), such as hydroxypropyl methyl cellulose acetate phthalate (HPMCAP), hydroxypropyl methyl cellulose acetate maleate (HPMCAM) or hydroxypropyl methylcellulose acetate succinate (HPMCAS); or ii) hydroxypropyl methyl cellulose phthalate (HPMCP); hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of 0.05 to 1.75, preferably of 0.10 to 1.50, more preferably of 0.15 to 1.25, and most preferably of 0.20 to 1.00. The esterified cellulose ethers generally have a degree of substitution of groups of formula —C(O)—R—COOA, such as succinoyl, of 0 to 1.6, preferably of 0.05 to 1.30, more preferably of 0.05 to 1.00, and most preferably of 0.10 to 0.70 or even 0.10 to 0.60.

The sum of i) the degree of substitution of aliphatic monovalent acyl groups and ii) the degree of substitution of groups of formula —C(O)—R—COOA is generally from 0.05 to 2.0, preferably from 0.10 to 1.4, more preferably from 0.20 to 1.15, most preferably from 0.30 to 1.10 and particularly from 0.40 to 1.00.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3) - M(H)}{M(COCH_3)}\right) -$$
$$\left(\% \text{ Succinoyl} * \frac{M(COC_2H_4COOH) - M(H)}{M(COC_2H_4COOH)}\right)$$

$$DS(Me) = \frac{\frac{\% \text{ MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$$DS(Succinoyl) = \frac{\frac{\% \text{ Succinoyl}}{M(Succinoyl)}}{\frac{\% \text{ cellulose backbone}}{M(AGU)}}$$

$M(MeO)=M(OCH_3)=31.03$ Da $M(HPO)=M(OCH_2CH(OH)CH_3)=75.09$ Da
$M(Acetyl)=M(COCH_3)=43.04$ Da $M(Succinoyl)=M(COC_2H_4COOH)=101.08$ Da
$M(AGU)=162.14$ Da $M(OH)=17.008$ Da $M(H)=1.008$ Da By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ethers of the present invention generally have a weight average molecular weight $M_w$ of 10,000 Dalton or more, preferably 30,000 Dalton or more, more preferably 50,000 Dalton or more, most preferably 80,000 Dalton or more, and particularly 100,000 Dalton or more. The esterified cellulose ethers of the present invention generally have a weight average molecular weight $M_w$ of up to 500,000, preferably up to 450,000 Dalton, more preferably up to 350,000 Dalton, even more preferably up to 250,000 Dalton, and particularly up to 200,000 Dalton or up to 180,000 Dalton.

The esterified cellulose ethers of the present invention typically have a Polydispersity $M_w/M_n$ of at least 1.3, more typically at least 1.5, and most typically at least 1.8 or at least 2.0. Moreover, the esterified cellulose ethers of the present invention typically have a Polydispersity of up to 4.0, preferably of up to 3.5, more preferably up to 3.0, even more preferably up to 2.8, and most preferably of up to 2.6. The Polydispersity $M_w/M_n$ is calculated based on the determination of the weight average molecular weight $M_w$ and the number average molecular weight $M_n$.

The esterified cellulose ethers of the present invention generally have a number average molecular weight $M_n$ of 5000 or more, preferably 10,000 Dalton or more, more preferably 30,000 Dalton or more, and most preferably 40,000 Dalton or more. The esterified cellulose ethers of the present invention generally have a number average molecular weight $M_n$ of up to 150,000 Dalton, preferably up to 110,000 Dalton, more preferably up to 90,000 Dalton, and most preferably up to 70,000 Dalton.

$M_w$ and $M_n$ are measured by SEC-MALLS using as mobile phase a mixture which has been produced by mixing 40 parts by volume of acetonitrile and 60 parts by volume of aqueous buffer containing 50 mM NaH$_2$PO$_4$ and 0.1 M NaNO$_3$. The mobile phase is adjusted to a pH of 8.0. SEC-MALLS stands for Size Exclusion Chromatography coupled with a mass sensitive Multi Angle Laser Light Scattering detector. The procedure is described in Journal of Pharmaceutical and Biomedical Analysis 56 (2011) 743-748. The measurement of $M_w$ and $M_n$ is described in more details in the Examples.

The esterified cellulose ethers of the present invention generally have a viscosity of up to 200 mPa·s, preferably up to 100 mPa·s, more preferably up to 50 mPa·s, even more preferably up to 30 mPa·s, most preferably up to 10 mPa·s, and particularly up to 5 mPa·s, measured as a 2.0 wt.-% solution of the esterified cellulose ether in 0.43 wt.-% aqueous NaOH at 20° C. Generally the viscosity is at least 1.2 mPa·s, typically at least 1.8 mPa·s, and more typically at least 2.4 mPa·s, measured as a 2.0 wt.-% solution of the esterified cellulose ether in 0.43 wt.-% aqueous NaOH at 20° C. The 2.0% by weight solution of the esterified cellulose ether is prepared as described in"Hypromellose Acetate Succinate, United States Pharmacopia and National Formulary, NF 29, pp. 1548-1550", followed by an Ubbelohde viscosity measurement according to DIN 51562-1:1999-01 (January 1999).

One important feature of the esterified cellulose ether of the present invention is its very low content of acetone-insoluble particles. More specifically, the esterified cellulose ether of the present invention has a content of not more than 0.85 weight percent, preferably not more than 0.50 weight percent, and more preferably not more than 0.35 weight percent of acetone-insoluble esterified cellulose ether particles, the weight percent acetone-insoluble esterified cellulose ether particles being based on the total weight of the esterified cellulose ether. Typically the esterified cellulose ether contains 0.05 weight percent or more, more typically 0.1 weight percent or more of acetone-insoluble esterified cellulose ether particles, based on the total weight of the esterified cellulose ether. The weight percent of acetone-insoluble esterified cellulose ether particles is determined by producing a mixture of 12.5 weight parts of esterified cellulose ether and 87.5 weight parts of acetone at 21° C. A way of determining the weight percent of acetone-insoluble esterified cellulose ether particles is described in more detail in the Examples. Expressed in other words, the weight percent of acetone-insoluble esterified cellulose ether particles is determined based on a 12.5 wt.-% solution of esterified cellulose ether in acetone at 21° C., where the term "12.5 wt.-% solution of esterified cellulose ether" refers to the total weight of dissolved and non-dissolved esterified cellulose ether particles. A very low concentration of acetone-insoluble esterified cellulose ether particles in a mixture of 10 to 20 weight parts, typically 12 to 15 weight parts of esterified cellulose ether and 80 to 90 weight parts, typically 85 to 88 weight parts of acetone is an important feature for efficient spray-drying. It is highly desirable to prepare and spray-dry solutions which comprise such high percentage of HPMCAS, e.g. as a carrier or a solubilizing agent for active ingredients, such as drugs, particularly drugs of poor water solubility.

Moreover, not more than 14 percent, preferably not more than 12 percent, more preferably not more than 10 percent, and most preferably not more than 8 percent of the above-mentioned small content of the acetone-insoluble esterified cellulose ether particles have a particle size of more than 90 micrometers, the percentage being based on the total number of acetone-insoluble esterified cellulose ether particles.

Preferably not more than 10 percent, more preferably not more than 8 percent, and most preferably not more than 4 percent of the above-mentioned small concentration of the acetone-insoluble esterified cellulose ether particles have a particle size of more than 130 micrometers, the percentage being based on the total number of acetone-insoluble esterified cellulose ether particles.

Surprisingly, the low weight percentage of acetone-insoluble esterified cellulose ether particles and the small particle size of these acetone-insoluble esterified cellulose ether particles can be achieved in a process for producing the esterified cellulose ether which comprises the steps of I. esterifying a cellulose ether with an aliphatic monocarboxylic acid anhydride or a dicarboxylic acid anhydride or combination thereof in the presence of an aliphatic carboxylic acid to produce a reaction product mixture comprising an esterified cellulose ether and the aliphatic carboxylic acid, II. optionally diluting the reaction product mixture obtained in step I, III. filtering the optionally diluted reaction product mixture and IV. precipitating the esterified cellulose ether from the filtered reaction product mixture by contacting the filtered reaction product mixture with water.

It is very surprising that the filtration of the optionally diluted reaction product mixture that comprises an aliphatic carboxylic acid, such as acetic acid, as reaction diluent, followed by precipitating the esterified cellulose ether from the filtered reaction product mixture by contacting the filtered reaction product mixture with water, reduces the amount and size of acetone-insoluble esterified cellulose ether particles. As illustrated by FIG. 1, part 1A, the reaction product mixture obtained by esterifying a cellulose ether with an aliphatic monocarboxylic acid anhydride or a dicarboxylic acid anhydride or a combination thereof in the presence of an aliphatic carboxylic acid, followed by optional dilution, is a clear solution; no non-dissolved particles are visible. FIG. 1, part 1A shows the solution in a glass container in a typical laboratory environment. No non-dissolved particles are visible, neither when the background is dark, like the laboratory table, nor when the background is bright, like the white wall of the laboratory. Hence, there is no apparent need to filter the solution. Moreover, no substantial difference is visible to the eye between the filtered and non-filtered solutions illustrated by FIG. 1. FIG. 1, part 1B, shows the solution which results from the filtration of the solution shown in FIG. 1, part 1A.

Also, it is surprising that filtering a reaction product mixture that is dissolved in an aliphatic carboxylic acid, such as acetic acid, reduces the amount and size of acetone-insoluble particles. Aliphatic carboxylic acids such as acetic acid are very different solvents than acetone. Moreover, it is surprising that the amount and size of acetone-insoluble particles can be reduced although the esterified cellulose ether is precipitated from the filtered reaction product mixture. It is generally known that in highly concentrated solutions, such as 10 to 20 wt.-%, typically 12 to 15 wt.-% in acetone, particle agglomeration occurs, which causes clogging when spray-drying a solution of a drug and an esterified cellulose ether. Hence, a simple step in the production of esterified cellulose ethers greatly improves the dissolution properties of esterified cellulose ethers in acetone and its utility for the producers of solid dispersions of active ingredients, such as drugs, in esterified cellulose ethers.

Procedures for esterifying a cellulose ether with an aliphatic monocarboxylic acid anhydride or a dicarboxylic acid anhydride or combination thereof in the presence of an aliphatic carboxylic acid are generally known in the art and, e.g., described in U.S. Pat. Nos. 3,435,027 and 4,226,981, in the International Patent Applications WO 2005/115330 and WO2013/148154, or in European Patent Application EP 0 219 426.

Preferably a cellulose ether is used as a starting material in step I of the process of the present invention which has the type of ether groups and the degree(s) of substitution of ether groups as described further above. The used cellulose ether generally has a viscosity of at least 1.2 mPa·s, typically at least 1.8 mPa·s, and more typically at least 2.4 mPa·s, measured as a 2 weight-% aqueous solution at 20° C. according to ASTM D2363-79 (Reapproved 2006). The used cellulose ether generally has a viscosity of up to 200 mPa·s, preferably up to 100 mPa·s, more preferably up to 50 mPa·s, even more preferably up to 30 mPa·s, most preferably up to 10 mPa·s, and particularly up to 5 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

Preferred aliphatic monocarboxylic acid anhydrides are selected from the group consisting of acetic anhydride, butyric anhydride and propionic anhydride. Preferred dicarboxylic acid anhydrides are selected from the group consisting of succinic anhydride, maleic anhydride and phthalic anhydride. If an aliphatic monocarboxylic acid anhydride and a dicarboxylic acid anhydride are used in combination, the two anhydrides may be introduced into the reaction vessel at the same time or separately one after the other. The amount of each anhydride to be introduced into the reaction vessel is determined depending on the desired degree of esterification to be obtained in the final product, usually being 1 to 10 times the stoichiometric amounts of the desired molar degree of substitution of the anhydroglucose units by esterification. If an anhydride of an aliphatic monocarboxylic acid is used, the molar ratio between the anhydride of an aliphatic monocarboxylic acid and the anhydroglucose units of the cellulose ether generally is 0.9 or more, and preferably 1 or more. The molar ratio between the anhydride of an aliphatic monocarboxylic acid and the anhydroglucose units of the cellulose ether generally is 8 or less, preferably 6 or less, and more preferably 4 or less. If an anhydride of a dicarboxylic acid is used, the molar ratio between the anhydride of a dicarboxylic acid and the anhydroglucose units of cellulose ether generally is 0.1 or more, and preferably 0.13 or more. The molar ratio between the anhydride of a dicarboxylic acid and the anhydroglucose units of cellulose ether generally is 1.5 or less, and preferably 1 or less. The molar number of anhydroglucose units of the cellulose ether utilized in the process of the present invention can be determined from the weight of the cellulose ether used as a starting material, by calculating the average molecular weight of the substituted anhydroglucose units from the DS(alkoxyl) and MS(hydroxyalkoxyl).

The esterification step I is conducted in an aliphatic carboxylic acid, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid is more than 50 percent, more preferably at least 75 percent, and even more preferably at least 90 percent, based on the total weight of the reaction diluent. Most preferably the reaction diluent consists of an aliphatic carboxylic acid. The molar ratio [aliphatic carboxylic acid/anhydroglucose units of cellulose ether] generally is from [4.9/1.0] to [11.5/1.0], preferably from [5.5/1.0] to [11.0/1.0], more preferably from [5.7/1.0] to [10.0/1.0].

The esterification reaction is generally conducted in the presence of an esterification catalyst, preferably in the presence of an alkali metal carboxylate, such as sodium acetate or potassium acetate. The amount of the alkali metal carboxylate is preferably 20 to 200 parts by weight of the alkali metal carboxylate per 100 parts by weight of the cellulose ether. The mixture is generally heated at 60° C. to 110° C., preferably at 70 to 100° C., for a period of time sufficient to complete the reaction, that is, typically from 2 to 25 hours, more typically from 2 to 8 hours.

In a preferred embodiment of the invention the esterification step I comprises the steps of (IA) dissolving or dispersing a cellulose ether and a first amount of alkali metal carboxylate in an aliphatic carboxylic acid, (IB) heating the obtained mixture to a temperature of 60° C. to 110° C., preferably 70 to 100° C., before, during or after adding an aliphatic monocarboxylic acid anhydride or a dicarboxylic acid anhydride or a combination thereof to the mixture obtained in step (IA), and allowing the esterification reaction to proceed, and (IC) before the esterification reaction in step (IB) is completed, adding a second amount of alkali metal carboxylate and allowing the esterification reaction to further proceed. Preferred cellulose ethers, alkali metal carboxylates, aliphatic carboxylic acids, aliphatic monocarboxylic acid anhydrides and dicarboxylic acid anhydrides for this preferred embodiment of the esterification process are those described further above. In step (IA) first the cellulose ether or first the alkali metal carboxylate or both simultaneously can be dissolved or dispersed in the aliphatic carboxylic acid. Preferably only 15 to 35 percent, more preferably only 20 to 30 percent of the total added amount of alkali metal carboxylate is added in step (IA). In step (IB) the esterification reaction is allowed to proceed for a period of time that is sufficient to partially complete the reaction, typically up to 60 minutes, more typically from 15 to 45 min. In step (IC) a second amount of alkali metal carboxylate is added to the reaction mixture and the esterification reaction is allowed to further proceed. Preferably 65 to 85 percent, more preferably 70 to 80 percent of the total added amount of alkali metal carboxylate is added in step (IC). The reaction mixture is typically kept at 60° C. to 110° C., preferably at 70 to 100° C., for an additional period of time sufficient to complete the reaction, that is, typically from 2 to 8 hours, more typically from 2 to 5 hours. In the preferred embodiment of the invention comprising steps (IA), (IB) and (IC), the total amount of alkali metal carboxylate added in steps (IA) and (IC) is preferably such that molar ratio [alkali metal carboxylate/anhydroglucose units of cellulose ether] is from [1.0/1.0] to [3.5/1.0], more preferably from [1.1/1.0] to [3.0/1.0], and most preferably from [1.9/1.0] to [2.5/1.0].

After completion of the esterification reaction in step I, the resulting reaction product mixture comprises the esterified cellulose ether, an aliphatic carboxylic acid used as a reaction medium, typically a reaction catalyst, such as an alkali metal carboxylate, typically residual amounts of one or more esterification agents and by-products, such as an aliphatic monocarboxylic acid and/or a dicarboxylic acid. The resulting reaction product mixture generally comprises from 3 to 60 weight percent of the esterified cellulose ether, from 20 to 90 weight percent of an aliphatic carboxylic acid, from 5 to 50 weight percent of a reaction catalyst, such as an alkali metal carboxylate, and from 0.1 to 30 weight percent of minor components, such as non-reacted anhydrides of an aliphatic monocarboxylic acid and/or of a dicarboxylic acid.

The reaction product mixture obtained in step I is optionally diluted in a step II. For example, some dilution and a reduction in viscosity of the reaction product mixture is achieved by quenching the reaction product mixture with a first amount of water. However, such quenching should be conducted without precipitating the esterified cellulose ether from the reaction product mixture. Alternatively, the viscosity of the reaction product mixture can be reduced by diluting the reaction product mixture with an organic solvent, such as the aliphatic carboxylic acid used as a reaction diluent like acetic acid. Before the optionally diluted reaction product is subjected to filtration, it can optionally be cooled or allowed to cool by other means.

In the filtration step III the reaction product mixture should generally have a temperature of 20° C. or more, preferably 30° C. or more, more preferably 40° C. or more, and most preferably 60° C. or more. If the reaction product mixture has not been diluted as described above, the reaction product mixture should generally have a temperature of 30° C. or more in the filtration step III. The temperature of the reaction product mixture generally is up to 110° C., preferably up to 100° C., and more preferably up to 90° C. during filtration.

Preferred filtration devices for conducting the filtration step III are basket strainers, filter cartridges or housings which are equipped with filter elements, filter bags or cartridges, such as standard cloth, depth or pleated filters including felt filters, microfiber and monofilament filters made from polypropylene, polyester, nylon, cotton or alike, or metal or stainless steel filters made from punched, slotted or chemically etched plates, wire screens, sintered plates, steel fleece or alike, or bulk material with an appropriate separation property, as sand, inert minerals synthetic solids etc. Typical companies for the supply of such filtration devices are LENZING Technik GmbH, Germany, (e.g. ViscoFil®), MAHLE Industry GmbH, Germany, (e.g. basket strain filters, automatic filters), FUHR GmbH, Gemany, (e.g. filter units, self-cleaning filters), or RusselFinex RUSSEL FINEX Inc., USA, (e.g. self-cleaning filters, Russell Eco Filter®). Most preferred is a filter housing equipped with a stainless steel filter made from punched or chemically etched plates or wire screens. The filtration step can be conducted at ambient pressure, but vacuum filtration or pressure filtration is preferred. The filtration device preferably has a screen having openings of 5 micrometers or more, and more preferably of 10 µm or more. Generally the screen has openings of up to 1000 micrometers, preferably of up to 500 µm, more preferably of up to 300 µm or 200 µm or 150 µm, most preferably of up to 100 µm or 90 µm, and for some applications up to 60 µm or 40 µm or 20 µm. A screen having openings of 90 micrometers has been found to provide an optimized combination of a very low content of acetone-insoluble esterified cellulose ether particles and high filtration efficiency. The filter media can be cleaned after usage or during continuous production in different ways, such as by rinsing with solvents or detergents, backwashing by the filtered fluid itself or mechanical cleaning by wipers, screws, pistons or alike.

In the subsequent step IV the esterified cellulose ether is precipitated from the filtered reaction product mixture by contacting the filtered reaction product mixture with water. The precipitation step IV can be conducted in a known manner, for example by contacting the reaction product mixture with a large volume of water, such as described in U.S. Pat. No. 4,226,981, International Patent Application WO 2005/115330 or European Patent Application EP 0 219 426. In a preferred embodiment of the invention the reaction product is precipitated from the reaction mixture as described in International Patent Application PCT/US13/030394, published as WO2013/148154, to produce an esterified cellulose ether in the form of a powder.

Another aspect of the present invention is a composition comprising a liquid diluent and one or more of the above described esterified cellulose ethers. The term "liquid diluent" as used herein means a diluent that is liquid at 25° C. and atmospheric pressure. The diluent is preferably an organic liquid diluent or a mixture of water and an organic liquid diluent. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. Most preferably, the liquid diluent is a ketone, such as acetone or a mixture of a ketone with another polar organic solvent.

The composition of the present invention comprising a liquid diluent and one or more of the above described esterified cellulose ethers is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers. The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The composition of the present invention preferably comprises from 1 to 40 weight percent, more preferably from 2.5 to 30 weight percent, most preferably from 5 to 25 weight percent, and particularly from 7 to 20 percent of at least one esterified cellulose ether as described above, from 40 to 99 weight percent, more preferably from 54.9 to 97.4 weight percent, most preferably from 65 to 94.5 weight percent and particularly from 70 to 92 percent of a liquid diluent described further above, and from 0 to 40 percent, preferably from 0.1 to 40 percent, most preferably from 0.5 to 25 percent, and particularly from 1 to 15 percent of an active ingredient, based on the total weight of the composition.

In one aspect of the invention the composition comprising at least one esterified cellulose ether as described above, one or more active ingredients and optionally one or more adjuvants can be used in liquid form, for example in the form of a suspension, a slurry, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with water as described above.

In another aspect of the invention the liquid composition of the present invention is used for producing a solid dispersion comprising at least one active ingredient, such as a drug described further above, at least one esterified cellulose ether as described above and optionally one or more adjuvants. The solid dispersion is produced by removing the liquid diluent from the composition.

One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing the liquid diluent from the mixture in a spray-drying apparatus where there is a strong driving force for evaporation of liquid diluent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25. Preferred liquid diluents are listed further above, particularly a ketone such as acetone or a mixture of a ketone with another polar organic solvent. The very low content of acetone-insoluble particles of the esterified cellulose ethers of the present invention and the small particle size of the residual amount of acetone-insoluble esterified cellulose ether particles make them very suitable for preparing a solid dispersion of an active ingredient in an esterified cellulose ether by spray-drying an above-mentioned composition comprising at least one esterified cellulose ether, a liquid diluent and at least one active ingredient. Clogging of the spray-drying devices can be significantly reduced, as compared to spray-drying of comparable compositions comprising known esterified cellulose ethers.

Alternatively, the solid dispersion of the present invention may be prepared by i) blending a) at least one esterified cellulose ether defined above, b) one or more active ingredients and c) one or more optional additives being different from components a) and b), and ii) subjecting the blend to extrusion. The term "extrusion" as used herein includes processes known as injection molding, melt casting and compression molding. Techniques for extruding, preferably for melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for extrusion. Useful devices for extrusion, specifically useful extruders, are known in the art. Alternatively, the components a), b) and optionally c) may be fed separately into the extruder and blended in the device before or during a heating step. After extrusion the extrudate may be easily shaped, molded, chopped, spheronized into beads, cut into strands, tableted or otherwise processed to the desired physical form. The extrudate can optionally be cooled to hardening and ground into a powdered form.

The solid dispersion of the present invention preferably comprises from 20 to 99.9 percent, more preferably from 30 to 98 percent, and most preferably from 60 to 95 percent of an esterified cellulose ether a) as described above, and preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, are one or more of the adjuvants c) which are different from components a) and b) and which are described in more detail below. The solid dispersion can comprise one or more of the esterified cellulose ethers a), one or more of the active ingredients b), and optionally one or more of the adjuvants c), however their total amount is generally within the above-mentioned ranges.

Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as, e.g. in the form of strands, pellets, granules, pills, tablets, caplets, microparticles, fillings of capsules or injection molded capsules or in the form of a powder, film, paste, cream, suspension or slurry.

The amount of the active ingredient in the dosage form is generally is at least 0.1 percent, preferably at least 1 percent, more preferably at least 3 percent, most preferably at least 5 percent, and generally up to 70 percent, preferably up to 50 percent, more preferably up to 30 percent, most preferably up to 25 percent, based on the total weight of the dosage form.

In another aspect of the invention the composition of the present invention comprising a liquid diluent and one or more of the above described esterified cellulose ethers may be used for coating dosage forms, such as tablets, granules, pellets, caplets, lozenges, suppositories, pessaries or implantable dosage forms, to form a coated composition. If the composition of the present invention comprises an active ingredient, such as a drug, drug layering can be achieved, i.e., the dosage form and the coating may comprise different active ingredients for different end-uses and/or having different release kinetics.

In yet another aspect of the invention the composition of the present invention comprising a liquid diluent and one or more of the above described esterified cellulose ethers may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

The following examples are for illustrative purposes only and are not intended to limit the scope of the present invention.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups ($-CO-CH_3$) and the ester substitution with succinoyl groups ($-CO-CH_2-CH_2-COOH$) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Viscosity of Hydroxypropyl Methyl Cellulose (HPMC) Samples

The viscosity of the HPMC samples is measured as a 2.0% by weight solution in water at 20° C.±0.1° C. The 2.0% by weight HPMC solution in water is prepared according to United States Pharmacopeia (USP 35, "Hypromellose", pages 3467-3469), followed by an Ubbelohde viscosity measurement according to DIN 51562-1:1999-01 (January 1999).

Viscosity of Hydroxypropyl Methyl Cellulose Acetate Succinate (HPMCAS)

The 2.0% by weight solution of the HPMCAS in 0.43 wt.-% aqueous NaOH is prepared as described in"Hypromellose Acetate Succinate, United States Pharmacopia and National Formulary, NF 29, pp. 1548-1550", followed by an Ubbelohde viscosity measurement at 20° C. according to DIN 51562-1:1999-01 (January 1999).

Determination of the Content of Acetone-Insoluble HPMCAS Particles

A 12.5 wt.-% solution of HPMCAS in acetone is prepared by adding 12.5 g of dry HPMCAS to 87.5 g of acetone followed by rolling the mixture on a roller for 12 hours at 21° C. 21.75 g of this solution is transferred into a weighted vial (volume 58 mL) and centrifuged with a Biofuge Stratos at 9124 rpm (9400×g) at for 30 min. while cooling to avoid heating of the mixture due to centrifugation. A clear liquid phase and solid fraction is obtained after centrifugation. Then the liquid phase is carefully removed by a syringe.

To remove remaining amounts of acetone and the HPMCAS dissolved therein entirely, 20 mL of acetone is added to the vial and carefully mixed with the solids. The spatula is purged with additional 15 mL of acetone to ensure that no insoluble particles are still attached to the spatula. Then the mixture is centrifuged again at 9124 rpm (9400×g) for 30 min. while cooling. Afterwards the liquid phase is carefully removed by a syringe. Acetone is evaporated from the remaining solids phase by keeping the open vial at 50° C. for 12 hours in a drying chamber. Then the vial is kept in an exsiccator for 45 min. at 21° C. The amount of acetone-insoluble particles in gram is the difference between the weight of the vial containing acetone-insoluble particles and the weight of the empty vial.

In the examples of the present invention the weight percent of acetone-insoluble esterified cellulose ether particles are measured in a mixture of 12.5 weight parts of esterified cellulose ether and 87.5 weight parts of acetone. Essentially the same results are obtained when measuring the weight percent of acetone-insoluble esterified cellulose ether particles in a 10 wt.-% solution of esterified cellulose ether in acetone, i.e. in a mixture of 10 weight parts of esterified cellulose ether and 90 weight parts of acetone. The difference between the acetone-insoluble contents in the two solutions of different concentration is less than 5%. For example, a first HPMCAS of the present invention had a) an acetone-insoluble content of 0.35% in a mixture of 12.5 wt. parts of HPMCAS and 87.5 wt. parts of acetone and b) an acetone-insoluble content of 0.34% in a mixture of 10.0 wt. parts of HPMCAS and 90.0 wt. parts of acetone. A second HPMCAS of the present invention had a) an acetone-insoluble content of 0.37% in a mixture of 12.5 wt. parts of HPMCAS and 87.5 wt. parts of acetone and b) an acetone-insoluble content of 0.36% in a mixture of 10.0 wt. parts of HPMCAS and 90.0 wt. parts of acetone.

Determination of the Particle Size of the Acetone-Insoluble Esterified Cellulose Ether Particles The particle sizes of the acetone-insoluble particles are determined by a laser diffraction particle size analyzer Beckman Coulter LS13320MW equipped with a universal liquid module (ULM2) and polarization intensity differential scattering (PIDS) module in a 15 wt. % acetone solution. A 15 wt. % solution of the esterified cellulose ether acetone is obtained by stiffing for 2 days at 21° C.

Determination of the Turbidity 1.5 weight % solutions in acetone of the hydroxyalkyl methyl cellulose acetate succinates of the present invention are prepared by mixing the hydroxyalkyl methyl cellulose acetate succinate with acetone and stirring the mixture at room temperature for 24 hours. The turbidity is analyzed with the Turbidimeter 2100AN (wolfram lamp, German catalogue number 47089-00) (Hach Company, Loveland, Colo., USA). The turbidity is the analysis of the scattered light through a sample cell (diameter: 24 mm) and is given in NTUs (nephelometric turbidity units) according to USEPA method 180.1. The analysis is performed against a formazin standard ranging from <0.1 NTU to 7500 NTU (StablCal™ catalogue number 2659505). A USEPA method 180.1 filter module (catalogue number 3031200) is used. The results given in the examples are the averages of 10 measurements.

Determination of $M_w$ and $M_n$

Mw and Mn are measured according to Journal of Pharmaceutical and Biomedical Analysis 56 (2011) 743-747 unless stated otherwise. The mobile phase was prepared by mixing mixture of 40 parts by volume of acetonitrile and 60 parts by volume of aqueous buffer containing 50 mM NaH2PO4 and 0.1 M NaNO3. The mobile phase was adjusted to a pH of 8.0. Solutions of the cellulose ether esters were filtered into a HPLC vial through a syringe filter of 0.45 µm pore size.

More specifically, the utilized Chemicals and solvents were:
Polyethylene oxide standard materials (abbreviated as PEOX 20 K and PEOX 30 K) were purchased from Agilent Technologies, Inc. Palo Alto, Calif., catalog number PL2083-1005 and PL2083-2005.

Acetonitrile (HPLC grade≥99.9%, CHROMASOL plus), catalog number 34998, sodium hydroxide (semiconductor grade, 99.99%, trace metal base), catalog number 306576, water (HPLC grade, CHROMASOLV Plus) catalog number 34877 and sodium nitrate (99.995%, trace metal base) catalog number 229938 were purchased from Sigma-Aldrich, Switzerland.

Sodium dihydrogen phosphate (≥99.999% TraceSelect) catalog number 71492. was purchased from FLUKA, Switzerland.

The normalization solution of PEOX20 K at 5 mg/mL, the standard solution of PEOX30 K at 2 mg/mL, and the sample solution of HPMCAS at 2 mg/mL were prepared by adding a weighed amount of polymer into a vial and dissolving it with a measured volume of mobile phase. All solutions were allowed to dissolve at room temperature in the capped vial for 24 h with stirring using a PTFE-coated magnetic stirring bar.

The normalization solution (PEOX 20k, single preparation, N) and the standard solution (PEOX30 K, double preparation, S1 and S2) were filtered into a HPLC vial through a syringe filter of 0.02 µm pore size and 25 mm diameter (Whatman Anatop 25, catalog number 6809-2002), Whatman.

The test sample solution (HPMCAS, prepared in duplicate, T1, T2) and a laboratory standard (HPMCAS, single preparation, LS) were filtered into a HPLC vial through a syringe filter of 0.45 µm pore size (Nylon, e.g. Acrodisc 13 mm VWR catalog number 514-4010).

Chromatographic condition and run sequence were conducted as described by Chen, R. et al.; Journal of Pharmaceutical and Biomedical Analysis 56 (2011) 743-748). The SEC-MALLS instrument set-up included a HP1100 HPLC system from Agilent Technologies, Inc. Palo Alto, Calif.; a DAWN Heleos II 18 angle laser light scattering detector and a OPTILAB rex refractive index detector, both from Wyatt Technologies, Inc. Santa Barbara, Calif. The analytical size exclusion column (TSK-GEL® GMPWXL, 300×7.8 mm) was purchased from Tosoh Bioscience. Both the OPTILAB and the DAWN were operated at 35° C. The analytical SEC column was operated at room temperature (24±5° C.). The mobile phase was a mixture of 40 volume parts of acetonitrile and 60 volume parts of aqueous buffer containing 50 mM NaH2PO4 and 0.1 M NaNO3 prepared as follows:

Aqueous buffer: 7.20 g of sodium dihydrogen phosphate and 10.2 g of sodium nitrate were added to 1.2 L purified water in a clean 2 L glass bottle under stirring until dissolution.

Mobile phase: 800 mL of acetonitrile were added to 1.2 L of the aqueous buffer prepared above, and stirred until a good mixture was achieved and the temperature equilibrated to ambient temperature.
The mobile phase was pH adjusted to 8.0 with 10M NaOH and filtered through a 0.2 m nylon membrane filter. The flow rate was 0.5 mL/min with in-line degassing. The injection volume was 100 µL and the analysis time was 35 min.

The MALLS data were collected and processed by Wyatt ASTRA software (version 5.3.4.20) using dn/dc value (refractive index increment) of 0.120 mL/g for HPMCAS. The light scattering signals of detector Nos. 1-4, 17, and 18) were not used in the molecular weight calculation. A representative chromatographic run sequence is given below: B, N, LS, S1 (5×), S2, T1 (2×), T2 (2×), T3 (2×), T4 (2×), S2, T5 (2×), etc., S2, LS, W, where, B represents blank injection of mobile phase, N1 represents normalization solution; LS represents a laboratory standard HPMCAS; S1 and S2 represent standard solutions one and two, respectively; T1, T2, T3, T4, and T5 represent test sample solutions and W represents water injection. (2×) and (5×) denote the number of injections of the same solution.

Both the OPTILAB and the DAWN were calibrated periodically according to the manufacturer's recommended procedures and frequency. A 100 µL injection of a 5 mg/mL polyethylene oxide standard (PEOX20 K) was employed for normalizing all angle light scattering detectors relative to 90-detector for each run sequence.

Use of this mono-dispersed polymer standard also enabled the volume delay between the OPTILAB and the DAWN to be determined, permitting proper alignment of the light scattering signals to the refractive index signal. This is necessary for the calculation of the weight-averaged molecular weight (Mw) for each data slice.

Production of HPMCAS According to Comparative Example A

Glacial acetic acid, acetic anhydride, a hydroxypropyl methylcellulose (HPMC), succinic anhydride and sodium acetate (water free) in the amounts listed in Table 1 below were utilized to produce HPMCAS. The HPMC had a methoxyl and hydroxypropoxyl substitution as listed in Table 2 below and a viscosity of about 3 mPa·s, measured as a 2% solution in water at 20° C. according to ASTM D2363-79 (Reapproved 2006). The HPMC is commercially available from The Dow Chemical Company as Methocel E3 LV Premium cellulose ether.

The HPMC (water free) was pre-dissolved at 85° C. in the acetic acid in a reactor together with 25% of the total amount of sodium acetate (water free) that was added to the reactor. Then the succinic anhydride and acetic anhydride were added to the reactor under stirring. After 30 min of reaction time the remaining 75% of the total amount of sodium acetate (water free) was added to the reactor. The reaction mixture was allowed to react for further 180 min. The reaction mixture had a temperature of 85° C.

After esterification, 0.28 L of water having a temperature of 23° C. was added to the reactor under stirring without precipitating the HPMCAS. 621 g of the reaction product mixture was removed from the reactor for the HPMCAS production according to Example 1. Then 1.2 L of water was added to the reactor under stirring to precipitate the HPMCAS. The precipitated product was removed from the reactor and washed with 8.5 L of water by applying high shear mixing using an Ultra-Turrax stirrer S50-G45 running at 5200 rpm. The product was isolated by filtration and dried at 55° C. overnight.

Production of HPMCAS According to Example 1

The 621 g of the transferred reaction product mixture of Comparative Example A was diluted with 2 L of glacial acetic acid directly after removal and was allowed to cool down to 23° C. FIG. 1A represents a photograph of the diluted reaction product mixture before filtration. The diluted reaction product mixture was filtered by passing it through a G4 glass filter screen having openings of 10 to 16 micrometers. FIG. 1B represents a photograph of the diluted reaction product mixture after filtration.

After the filtration 8 L of water having a temperature of 23° C. was added to the reactor under stirring to precipitate the HPMCAS. The precipitated product was washed with 12 L of water by applying high shear mixing using an Ultra-Turrax stirrer S50-G45 running at 5200 rpm. The product was isolated by filtration and dried at 55° C. overnight.

Production of HPMCAS According to Comparative Example B

Glacial acetic acid, acetic anhydride and succinic anhydride were introduced in the amounts listed in Table 1 below into a reaction vessel under thorough stirring. Then the mixture was heated at 55° C. with agitation until the succinic anhydride was dissolved. Then sodium acetate (water free) and the same HPMC as in Comparative Example A were introduced in the amounts listed in Table 1. The reaction mixture was allowed to react for 180 min at 85° C.

After esterification, 0.28 L of water having a temperature of 23° C. was added to the reactor under stirring without precipitating the HPMCAS. 607 g of the reaction product mixture was removed from the reactor for the HPMCAS production according to Example 2. Then 1.2 L of water was added to the reactor under stirring to precipitate the HPMCAS. The precipitated product was removed from the reactor and washed with 10.5 L of water by applying high shear mixing using an Ultra-Turrax stirrer S50-G45 stirrer running at 5200 rpm. The product was isolated by filtration and dried at 55° C. overnight.

Production of HPMCAS According to Example 2

The 607 g of the transferred reaction product mixture of Comparative Example B was diluted with 2 L of glacial acetic acid directly after removal and was allowed to cool down to 23° C. The diluted reaction product mixture was filtered by passing it through a G4 glass filter having openings of 10 to 16 micrometers.

After the filtration 8 L of water having a temperature of 23° C. was added to the reactor under stirring to precipitate the HPMCAS. The precipitated product was washed with 8 L of water by applying high shear mixing using an Ultra-Turrax stirrer S50-G45 running at 5200 rpm. The product was isolated by filtration and dried at 55° C. overnight.

Production of HPMCAS According to Comparative Examples C and D (Corresponding to Examples 1 and 2 of the Co-Pending U.S. Provisional Patent Application Ser. No. 61/942,371, Filed 20 Feb. 2014)

Glacial acetic acid, acetic anhydride, a hydroxypropyl methylcellulose (HPMC), succinic anhydride and sodium acetate (water free) in the amounts listed in Table 1 below were utilized to produce HPMCAS. The HPMC had a methoxyl and hydroxypropoxyl substitution as listed in Table 2 below and a viscosity of about 3 mPa·s, measured as a 2% solution in water at 20° C. according to ASTM D2363-79 (Reapproved 2006). The HPMC is commercially available from The Dow Chemical Company as Methocel E3 LV Premium cellulose ether.

230 g of HPMC (water free) was pre-dissolved at 85° C. in 170 g of acetic acid together with 50 g of sodium acetate (water free). Then 38.9 g of succinic anhydride and 170 g of acetic anhydride were added to the reactor under stirring. After 30 min of reaction time 150 g of sodium acetate (water free) was added to the reactor. In Comparative Example C the reaction mixture was allowed to react for further 120 min.; in Comparative Example D the reaction mixture was allowed to react for further 180 min.

After esterification, in each of the Comparative Examples C and D, 2.3 L of water was added to the reactor under stirring to precipitate the HPMCAS. The precipitated product was removed from the reactor and washed with 14-19 L of water by applying high shear mixing using an Ultra-Turrax stirrer S50-G45 running at 5200 rpm. The product was isolated by filtration and dried at 50° C. overnight.

Production of HPMCAS According to Comparative Examples E and F

Comparative Examples E and F correspond to Examples 3 and 4 of International Patent Application WO2014/031422. Comparative Examples E and F (Examples 3 and 4 of International Patent Application WO2014/031422) have a weight average molecular weight $M_w$ that is comparable to the HPMCAS of Examples 1 and 2 of the present invention and a low turbidity as 1.5 weight percent solution in acetone. Comparative Examples E and F illustrate that a low turbidity in acetone solutions does not correlate with a low content of acetone-insoluble HPMCAS in a mixture of 10 weight percent esterified cellulose ether and 90 weight percent acetone.

Comparative Examples E and F were produced by introducing glacial acetic acid, acetic anhydride, a hydroxypropyl methylcellulose (HPMC), succinic anhydride and sodium acetate (water free) in the amounts listed in Table 1 below into a reaction vessel under thorough stirring. The same HPMC as in Example 1 was used. The mixture was heated at 85° C. with agitation for 3 hours to effect esterification. 1.8 L of water was added to the reactor under stirring to precipitate the HPMCAS. The precipitated product was removed from the reactor and washed with 16 L of water by applying high shear mixing using an Ultra-Turrax stirrer S50-G45 running at 5200 rpm. The product was isolated by filtration and dried at 50° C. The product was then thoroughly washed by repeatedly slurrying the product in excess water using the Ultra-Turrax stirrer S50-G45 and isolating the product by filtration. The washed product was dried again at 50° C.

Comparative Examples G to I

As disclosed in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed below.

Properties of AQOAT polymers as listed in WO 2011/159626

| | Designation of analyzed commercial samples: Comparative Example | | |
|---|---|---|---|
| | G | H | I |
| | Published Composition of AQOAT polymers (wt %) | | |
| Substituent content | L-Grade | M-Grade | H-Grade |
| Methoxyl | 20.0-24.0 | 21-0-25.0 | 22.0-26.0 |
| Hydroxypropoxyl | 5.0-9.0 | 5.0-9.0 | 6.0-10.0 |
| Acetyl | 5.0-9.0 | 7.0-11.0 | 10.0-14.0 |
| Succinoyl | 14.0-18.0 | 10-14 | 4.0-8.0 |

Samples of the commercially available materials were analyzed as described further above.

The properties of the HPMCAS produced according to Examples 1-2 and comparative Examples A-I are listed in Tables 2 and 3 below.

In Tables 2 and 3 below the abbreviations have the following meanings:

$DS_M$=DS(methoxyl): degree of substitution with methoxyl groups;

$MS_{HP}$=MS(hydroxypropoxyl): molar subst. with hydroxypropoxyl groups;

$DOS_{Ac}$: degree of substitution of acetyl groups;

$DOS_s$: degree of substitution of succinoyl groups.

The results in Table 3 below illustrate that the esterified cellulose ethers of the present invention have a combination of a) a very low content of acetone-insoluble esterified cellulose ether particles and b) a small particle size of the acetone-insoluble esterified cellulose ether particles. This is highly desirable for many applications that require a high quality of esterified cellulose ethers, such as spray-drying a solution of a drug and an esterified cellulose ether.

TABLE 1

| (Comparative) Example | HPMC* g | HPMC* Mol | acetic acid G | acetic acid HPMC | Succinic anhydride g mol/mol | Succinic anhydride HPMC | Acetic anhydride g mol/mol | Acetic anhydride HPMC | Sodium acetate g mol/mol | Sodium acetate HPMC | Heating at 85° C. hours |
|---|---|---|---|---|---|---|---|---|---|---|---|
| A | 200 | 0.99 | 452 | 7.6 | 33.8 | 0.34 | 147 | 1.52 | 174 | 2.15 | 3 |
| 1 | 200 | 0.99 | 452 | 7.6 | 33.8 | 0.34 | 147 | 1.52 | 174 | 2.15 | 3 |
| B | 200 | 0.99 | 452 | 7.6 | 33.8 | 0.34 | 147 | 1.52 | 174 | 2.15 | 3 |
| 2 | 200 | 0.99 | 452 | 7.6 | 33.8 | 0.34 | 147 | 1.52 | 174 | 2.15 | 3 |
| C | 230 g | 1.14 | 513 | 7.6 | 38.9 | 0.34 | 170 | 1.53 | 200 | 2.15 | 2 |
| D | 230 g | 1.14 | 513 | 7.6 | 38.9 | 0.34 | 170 | 1.53 | 200 | 2.15 | 3 |
| E | 195 | 0.97 | 440 | 7.6 | 40.0 | 0.42 | 200 | 2.12 | 120 | 1.52 | 3 |
| F | 195 | 0.97 | 440 | 7.6 | 40.0 | 0.42 | 200 | 2.12 | 195 | 2.47 | 3 |

*calculated on the dried basis

TABLE 2

| Table 2 (Comp.) Example | Molecular weight (kDA) $M_w$ | Molecular weight (kDA) $M_n$ | Recovery Rate (%) | 2% viscosity* (mPa·s) | Ether Substitution Methoxyl (%) | Ether Substitution Hydroxy-propoxyl, % | Ester substitution Acetyl (%) | Ester substitution Succinoyl (%) | Ether Substitution $DS_M$ | Ether Substitution $MS_{HP}$ | Ester substitution $DOS_{Ac}$ | Ester substitution $DOS_s$ |
|---|---|---|---|---|---|---|---|---|---|---|---|---|
| A | 182 | 77 | 95.8 | 2.83 | 23.1 | 7.3 | 9.6 | 11.7 | 1.92 | 0.25 | 0.57 | 0.30 |
| 1 | 220 | 102 | 95.7 | 3.12 | 22.9 | 7.4 | 9.6 | 11.8 | 1.90 | 0.25 | 0.58 | 0.30 |
| B | 129 | 45 | 96 | 2.78 | 23.3 | 7.4 | 8.7 | 12 | 1.92 | 0.25 | 0.52 | 0.30 |
| 2 | 150 | 58 | 100 | 3.02 | 23.1 | 7.4 | 8.8 | 12.1 | 1.91 | 0.25 | 0.52 | 0.31 |
| C | 126 | 57 | 102 | 2.74 | 23.6 | 7.5 | 8.4 | 11.3 | 1.92 | 0.25 | 0.49 | 0.28 |
| D | 139 | 63 | 103 | 2.65 | 23.5 | 7.4 | 8.9 | 11.6 | 1.93 | 0.25 | 0.53 | 0.29 |
| E | 95 | 28 | 100 | 2.66 | 23.1 | 7.5 | 9.7 | 11.7 | 1.92 | 0.26 | 0.58 | 0.30 |
| F | 144 | 38 | 98 | 2.64 | 22.9 | 7.5 | 9.9 | 12.3 | 1.93 | 0.26 | 0.60 | 0.32 |
| G | 152 | 35 | 100 | 3.0 | 22.5 | 7.0 | 8.1 | 14.7 | 1.9 | 0.24 | 0.49 | 0.38 |
| H | 124 | 28 | 97.9 | 2.94 | 23.1 | 7.4 | 9.3 | 11.1 | 1.89 | 0.25 | 0.55 | 0.28 |
| I | 135 | 29 | 96.7 | 2.89 | 23.6 | 7.5 | 11.9 | 7.6 | 1.91 | 0.25 | 0.70 | 0.19 |

TABLE 3

| Table 2 (Comp.) Example | Molecular weight (kDA) $M_w$ | Molecular weight (kDA) $M_n$ | Ether Substitution Methoxyl (%) | Ether Substitution Hydroxy-Propoxyl, % | Ester substitution Acetyl (%) | Ester substitution Succinoyl (%) | Turbidity 1.5 wt.-% in acetone [NTU] | Acetone-insoluble HPMCAS (wt. %)[1] | % of acetone insoluble HPMCAS particles having a size of more than >90 μm | % of acetone insoluble HPMCAS particles having a size of more than >130 μm |
|---|---|---|---|---|---|---|---|---|---|---|
| A | 182 | 77 | 23.1 | 7.3 | 9.6 | 11.7 | 13.9 | 0.35 | 76.4 | 72.3 |
| 1 | 220 | 102 | 22.9 | 7.4 | 9.6 | 11.8 | 12.1 | 0.11 | 0.0 | 0.0 |
| B | 129 | 45 | 23.3 | 7.4 | 8.7 | 12 | 26.0 | 0.98 | 28.3 | 23.1 |
| 2 | 150 | 58 | 23.1 | 7.4 | 8.8 | 12.1 | 18.3 | 0.33 | 0.1 | 0.0 |
| C | 126 | 57 | 23.6 | 7.5 | 8.4 | 11.3 | 19.7 | 0.11 | 15.4 | 11.9 |
| D | 139 | 63 | 23.5 | 7.4 | 8.9 | 11.6 | 22.9 | 0.22 | 21.8 | 18.6 |
| E | 95 | 28 | 23.1 | 7.5 | 9.7 | 11.7 | 13.4 | 1.19 | 49.8 | 43.6 |
| F | 144 | 38 | 22.9 | 7.5 | 9.9 | 12.3 | 12.4 | 0.99 | 18.2 | 11.6 |
| G | 152 | 35 | 22.5 | 7.0 | 8.1 | 14.7 | 39.4 | 1.36 | not assessed | not assessed |
| H | 124 | 28 | 23.1 | 7.4 | 9.3 | 11.1 | 53.9 | 1.26 | not assessed | not assessed |
| I | 135 | 29 | 23.6 | 7.5 | 11.9 | 7.6 | 42.4 | 1.23 | not assessed | not assessed |

[1]In a mixture of 12.5 weight percent esterified cellulose ether and 87.5 weight percent acetone at 21° C.

The invention claimed is:

1. An esterified cellulose ether having
    i) as ester groups aliphatic monovalent acyl groups or groups of the formula —C(O)—R—COOA or a combination of aliphatic monovalent acyl groups and groups of the formula —C(O)—R—COOA, wherein R is a divalent aliphatic or aromatic hydrocarbon group and A is hydrogen or a cation, and
    ii) a content of not more than 0.85 weight percent acetone-insoluble esterified cellulose ether particles, when the esterified cellulose ether is present in a mixture of 12.5 weight parts of esterified cellulose ether and 87.5 weight parts of acetone at 21° C., the weight percent acetone-insoluble esterified cellulose ether particles being based on the total weight of the esterified cellulose ether, wherein iii) not more than 14 percent of the acetone-insoluble esterified cellulose ether particles have a particle size of more than 90 micrometers, the percentage being based on the total number of acetone-insoluble esterified cellulose ether particles.

2. The esterified cellulose ether of claim 1 having a content of not more than 0.50 weight percent acetone-insoluble esterified cellulose ether particles, based on the total weight of the esterified cellulose ether.

3. The esterified cellulose ether of claim 1 wherein not more than 10 percent of the acetone-insoluble esterified cellulose ether particles have a particle size of more than 90 micrometers, the percentage being based on the total number of acetone-insoluble esterified cellulose ether particles.

4. The esterified cellulose ether of claim 1 wherein the aliphatic monovalent acyl groups are acetyl, propionyl or butyryl groups and the groups of the formula —C(O)—R—COOA are —C(O)—$CH_2$—$CH_2$—COOA, —C(O)—CH=CH—COOA, or —C(O)—$C_6H_4$—COOA.

5. The esterified cellulose ether of claim 1 being hydroxypropyl methyl cellulose acetate succinate.

6. A process for producing the esterified cellulose ether of claim 1 comprising the steps of
    I. esterifying a cellulose ether with an aliphatic monocarboxylic acid anhydride or a dicarboxylic acid anhydride or combination thereof in the presence of an aliphatic carboxylic acid to produce a reaction product mixture comprising an esterified cellulose ether and the aliphatic carboxylic acid,
    II. optionally diluting the reaction product mixture obtained in step I,
    III. filtering the optionally diluted reaction product mixture, and
    IV. precipitating the esterified cellulose ether from the filtered reaction product mixture by contacting the filtered reaction product mixture with water.

7. The process of claim 6 wherein in the reaction product mixture obtained in step I or II is filtered through a screen having openings of up to 1000 micrometers.

8. The process of claim 6 wherein the reaction product mixture obtained in step I is mixed with a first amount of water without precipitating the esterified cellulose ether from the reaction product mixture or with an aliphatic carboxylic acid prior to filtration in step III.

9. The process of claim 6 wherein the esterification step I comprises the steps of
    (IA) dissolving or dispersing a cellulose ether and a first amount of alkali metal carboxylate in an aliphatic carboxylic acid,
    (IB) heating the obtained mixture to a temperature of 60° C. to 110° C. before, during or after adding an aliphatic monocarboxylic acid anhydride or a dicarboxylic acid anhydride or a combination thereof to the mixture obtained in step (IA), and allowing the esterification reaction to proceed, and
    (IC) before the esterification reaction in step (IB) is completed, adding a second amount of alkali metal carboxylate and allowing the esterification reaction to further proceed.

10. The process of claim 9 wherein the first amount of alkali metal carboxylate added in step (IA) is 15 to 35 percent and the second amount of alkali metal carboxylate added in step (IB) is 65 to 85 percent, based on the total amount of added alkali metal carboxylate in the process.

11. A composition comprising a liquid diluent and at least one esterified cellulose ether of claim 1.

12. A solid dispersion comprising at least one active ingredient in at least one esterified cellulose ether of claim 1.

13. A dosage form being coated with the esterified cellulose ether of claim 1.

14. A capsule shell comprising the esterified cellulose ether of claim 1.

* * * * *